US010926215B2

(12) United States Patent
Low et al.

(10) Patent No.: US 10,926,215 B2
(45) Date of Patent: Feb. 23, 2021

(54) PROCESS FOR DRYING A GAS STREAM COMPRISING 2,3,3,3 TETRAFLUOROPROPENE

(71) Applicant: MEXICHEM AMANCO HOLDING S.A. DE C.V., Tlalnepantla (MX)

(72) Inventors: Robert Elliott Low, Flintshire (GB); Stuart Corr, Cheshire (GB)

(73) Assignee: Mexichem Amanco Holding S.A. de C.V., Tlalnepantla (MX)

( * ) Notice: Subject to any disclaimer, the term of this patent is extended or adjusted under 35 U.S.C. 154(b) by 0 days.

(21) Appl. No.: 16/701,879

(22) Filed: Dec. 3, 2019

(65) Prior Publication Data

US 2020/0101417 A1 Apr. 2, 2020

Related U.S. Application Data

(63) Continuation of application No. 16/189,383, filed on Nov. 13, 2018, now Pat. No. 10,493,399, which is a (Continued)

(30) Foreign Application Priority Data

Jun. 14, 2006 (GB) ..................................... 0611742

(51) Int. Cl.
    C07C 21/18    (2006.01)
    B01D 53/26    (2006.01)
    C07C 17/389   (2006.01)

(52) U.S. Cl.
    CPC .......... B01D 53/261 (2013.01); C07C 17/389 (2013.01); C07C 21/18 (2013.01)

(58) Field of Classification Search
    CPC ...... B01D 53/261; C07C 17/389; C07C 21/18
    See application file for complete search history.

(56) References Cited

U.S. PATENT DOCUMENTS 3,625,866 A  12/1971  Conde
4,906,796 A   3/1990  Yates
             (Continued)

FOREIGN PATENT DOCUMENTS

EP      974633      1/2000
EP     1116706 A    7/2001
             (Continued)

OTHER PUBLICATIONS

Henne et al., "Fluorinated Derivatives of Propane and Propylene", American Chem Society, Mar. 1946, vol. 68, pp. 496-497.
(Continued)

*Primary Examiner* — Filip Zec
(74) *Attorney, Agent, or Firm* — Brinks Gilson & Lione

(57) ABSTRACT

A method of drying a fluid comprising a fluoropropene, which method comprises the step of contacting the fluid with a desiccant comprising a molecular sieve having openings which have a size across their largest dimension of from about 3 Å to about 5 Å. A heat transfer device comprising a heat transfer fluid comprising a fluoropropene, and a desiccant comprising a molecular sieve having openings which have a size across their largest dimension of from about 3 Å to about 5 Å. Preferably, the fluoropropene is R134yf or R-1225ye.

21 Claims, 1 Drawing Sheet

Desiccant Moisture Content

Related U.S. Application Data continuation of application No. 12/308,327, filed as application No. PCT/GB2007/002223 on Jun. 14, 2007, now Pat. No. 10,130,909.

(56) References Cited

U.S. PATENT DOCUMENTS

| | | | |
|---|---|---|---|
| 5,233,107 A | 8/1993 | Rolf-Michael | |
| 5,454,966 A | 10/1995 | Thomas et al. | |
| 5,514,633 A | 5/1996 | Noguchi et al. | |
| 5,742,066 A | 4/1998 | Cavestri | |
| 5,910,161 A | 6/1999 | Fujita | |
| 6,313,059 B1 | 11/2001 | Lavin et al. | |
| 6,403,847 B1 | 6/2002 | Nakada et al. | |
| 6,589,444 B2 | 7/2003 | Thomas et al. | |
| 7,041,264 B2 | 5/2006 | Horiba et al. | |
| 7,094,935 B2 | 8/2006 | Suzuki et al. | |
| 7,423,103 B2 | 9/2008 | Stavens | |
| 8,420,873 B2* | 4/2013 | Takahashi | C07C 17/383 570/202 |
| 8,951,431 B2* | 2/2015 | Hulse | C07C 17/389 252/67 |
| 9,012,703 B2 | 4/2015 | Sharratt | |
| 2003/0157009 A1 | 8/2003 | Corr et al. | |
| 2004/0089839 A1 | 5/2004 | Thomas et al. | |
| 2006/0043331 A1 | 3/2006 | Shankland et al. | |
| 2008/0011159 A1 | 1/2008 | Thomas et al. | |
| 2008/0098755 A1 | 5/2008 | Singh | |
| 2008/0116417 A1* | 5/2008 | Samuels | C09K 5/045 252/68 |

FOREIGN PATENT DOCUMENTS

| | | |
|---|---|---|
| EP | 1116706 B | 12/2004 |
| JP | 10443346 | 2/1989 |
| JP | 03072437 A | 3/1991 |
| JP | H4110388 | 4/1992 |
| JP | 6327968 | 11/1994 |
| JP | 9241189 | 9/1997 |
| JP | 1997241189 | 9/1997 |
| JP | 11293273 | 10/1999 |
| JP | 2000-39235 | 2/2000 |
| JP | 2001523561 | 11/2001 |
| JP | 2003-533447 | 11/2003 |
| JP | 2004339187 | 12/2004 |
| WO | WO99/026708 | 6/1999 |
| WO | WO01/017646 | 3/2001 |
| WO | WO01/83411 | 11/2001 |
| WO | WO01/83411 A | 11/2001 |
| WO | WO04/037913 | 5/2004 |
| WO | WO04/074225 | 9/2004 |
| WO | WO05/042451 | 5/2005 |
| WO | WO05/067554 | 7/2005 |
| WO | WO05/103191 | 11/2005 |
| WO | WO07/002625 | 1/2007 |
| WO | WO07/053697 | 5/2007 |

OTHER PUBLICATIONS

Molecular Sieve Dessicant, Ford Motor Company Engineering Material, Specification, Aug. 14, 2002, 4 pgs.

Chapter 6 of 2002 Ashrae Handbook, Refrigeration, 17 pgs, date unknown.

Extract from Chapter 2 of French Oil Institute Publication (with English translation), 8 pgs., 1998.

ACRIB document relating to F-Gas regulation and GWP, 2 pgs, May 2015.

Raabe G., May 17, 2012, J Phys Chem B, Molecular Modeling of Fluoropropene Refrigerants, Abstract.

Kawahira, M. Japanese Association of Refrigeration, 1981, pp. 188-191 (partial English Translation).

Product Catalog of Molecular Sieve, Union Showa K.K (partial English Translation, p. 4).

IPRP PCT/GB2007/00223 Dec. 16, 2008.

Banks et al., "Organofluorine Chemistry", 1994, Plenum Press, Chapter 3.

Breck, "Zeolite Molecular Sieves", 1974, John Wiley & Sons, pp. 64-67 and 133-180.

ASHRAE Refrigeration Handbook 2002, Chapter 6.

Breck, Zeolite Molecular Sieves, 1974, John Wiley & Sons, pp. 596-610, 633-637, 699-709.

CFCs, The Day After, International Institute of Refrigeration, Sep. 1994.

Dyer, An Introduction to Zeolite Molecular Sieves, John Wiley & Sons Ltd. pgd 93-97 and 102-106, 1988.

Lautensack et al., Molecular Sieve a Refrigerant Desiccant, Refrigerating Engineering, pp. 33-36, May 1957.

Pfenninger, Manufacture and Use of Zeolites for Adsorption Processes in Molecular Sieves: Science and Technology, vol. 2, 163-198, 1998.

Uop Molecular Sieves, Technical Brochure 1988.

Wauquier, Procedes de separation, Publications de l'Institut Fracais du Petrole, pp. 542-544 and 585-589, 1998 (english translation).

* cited by examiner

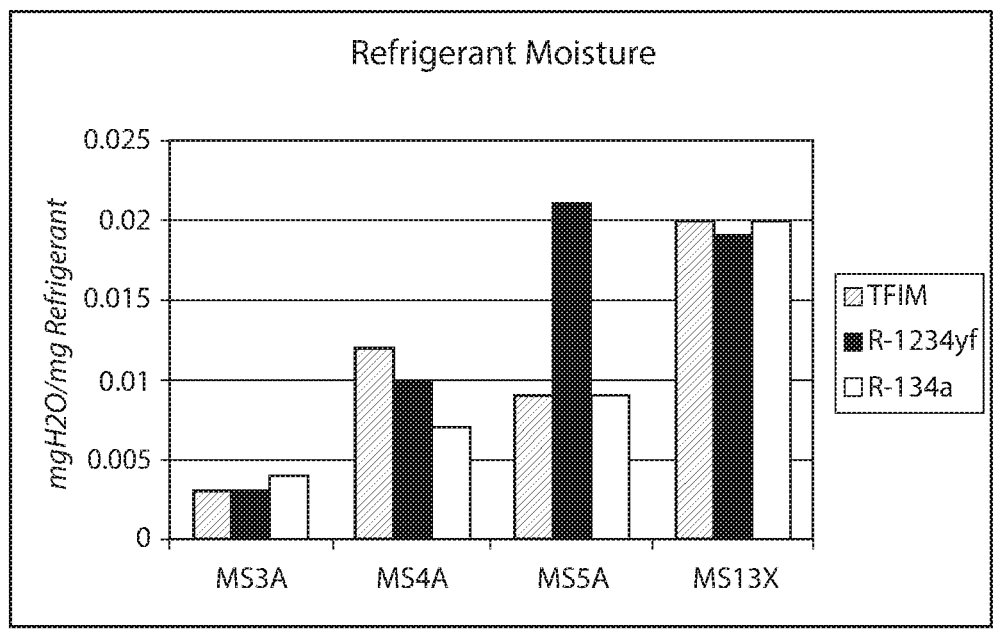
Figure 1. Refrigerant Moisture Content
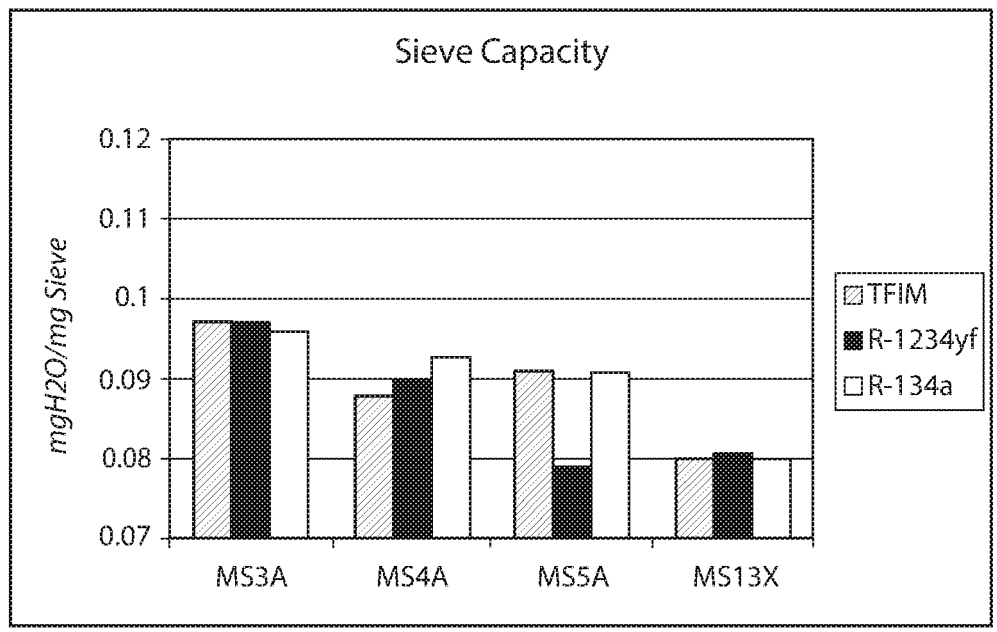
Figure 2. Desiccant Moisture Content

PROCESS FOR DRYING A GAS STREAM COMPRISING 2,3,3,3 TETRAFLUOROPROPENE

RELATED APPLICATIONS

This application is a continuation of U.S. application Ser. No. 16/189,383 filed 13 Nov. 2018 (now U.S. Pat. No. 10,493,399), which is a continuation of U.S. application Ser. No. 12/308,327 filed 19 Oct. 2009 (now U.S. Pat. No. 10,130,909), which is a 371 of international application Serial No. PCT/GB2007/002223 filed 14 Jun. 2007.

BACKGROUND OF THE INVENTION

The invention relates generally to desiccants for drying fluids containing fluorinated propenes. In particular, the invention relates to the use of desiccants comprising molecular sieves having defined pore sizes.

It is generally recognised that it is important to control the levels of water present within vapour compression refrigeration systems that utilise halogenated fluids as the heat transfer media. High levels of moisture in such systems can result in a number of reliability and performance problems. With levels approaching or above those where free-phase water can form, solid clathrates or ice crystals can form. Solid clathrates can form at temperatures above that of the normal freezing point of water. These solid materials can act to restrict refrigerant flow, particularly through the expansion device, typically a valve, orifice tube or capillary tube, that is used to regulate refrigerant flow through the system.

At lower levels of moisture, many polymeric materials found in hermetic compressor systems, in particular those associated with the hermetic electric motor insulation such as nylon and PET, may be subject to hydrolytic degradation leading to motor burn-out and premature system failure. Moisture may also act to corrode metallic components of the system and contribute to the phenomenon of copper-plating where copper is transported from components constructed of copper and deposited onto ferrous-alloy surfaces. When these surfaces are in the compressor, such as valves and piston elements, this deposition acts to reduce mechanical clearances and may eventually lead to seizure.

In order to minimise the detrimental effects of moisture in refrigeration systems, these systems incorporate a dryer material in order to selectively absorb moisture from the circulating fluid. Traditionally these driers have been manufactured from a number of materials including activated alumina, silica gel and aluminosilicate molecular sieves (zeolites). The desiccant is usually used in the form of a porous moulded core consisting one or more of the desiccant materials, or in the form of a loose-fill of beads or pellets of desiccant. In either case, the desiccant is held within a cartridge and the refrigerant, in liquid or vapour form, is caused to pass through the cartridge in contact with the desiccant.

The zeolite molecular sieves are of particular interest since they can combine a high capacity for moisture retention with the capability of reducing the moisture content of the refrigeration fluid to low levels in order to achieve satisfactory desiccant performance with such molecular sieves, it is important to minimise the competitive absorption of refrigerant. This is normally achieved by selecting a molecular sieve with a pore-opening dimension that is sufficiently small such that refrigerant absorption is minimised but which is sufficiently wide to maintain satisfactory rates of moisture absorption. This minimisation of refrigerant absorption is also required in order to avoid degradation of the refrigerant through reaction within the molecular sieve channels.

Whilst moisture control within a refrigeration system is clearly important, it is also necessary to dry refrigerant fluids as part of their manufacturing process. In this way, any moisture that may be incorporated into the refrigerant through steps of the manufacturing process, e.g, by aqueous scrubbing, may be removed before the fluid is packaged or placed in receiver vessels. Drying the fluid thus avoids any corrosion or icing issues associated with handling and storing the fluids and helps to ensure that subsequent introduction of the fluid into a refrigeration circuit does not introduce excessive levels of moisture that may overload the drying capacity of any in-line system desiccant.

The Montreal Protocol brought about the replacement of the traditional chlorofluorocarbon (CFC) and hydrochlorofluorocarbon (HCFC) refrigerants including R-12 (dichlorodifluoromethane), R-22 (chlorodifluoro-methane) and R-502, an azeotropic mixture of R-22 and R-115 (chloropentafluoroethane). These substances have generally been replaced by hydrofluorocarbon (HFC) refrigerants of general formula (where $C_nH_xF_y$ (where n=1 to 3, x=1 to (2n−1) and (x+y)=2n+2) and their mixtures, These refrigeration fluids are generally used in combination with a synthetic compressor lubricant, most often an ester, a polyalkyleneglycol (PAG) or a polyvinyl ether (PVE). Both the HFC refrigerants and their synthetic lubricants are more polar and more hygroscopic than the traditional combination of CFC and HCFC refrigerants with their mineral oil or synthetic hydrocarbon compressor lubricants.

One of the most common refrigerants used historically was R-12. This was replaced by R-134a (1,1,1,2-tetrafluoroethane) in the 1990s in the majority of its application areas. One of the single largest application areas for R-134a is in automotive air conditioning systems where it is used in conjunction with a polyalkylene glycol compressor lubricant. Other application areas include domestic and industrial refrigeration where it is generally used in conjunction with an ester or PVE compressor lubricant, typically an ester from the family of neopentylpolyol esters (POEs). R-134a is also a component of refrigerant blends that have been used to replace R-22 and R-502 in commercial and residential freezing, refrigeration and air conditioning applications.

The global warming potential (GWP) of R-134a, 1300 relative to $CO_2$ on a 100-year timescale, has led to pressure to develop alternative ozone-benign refrigerants having a reduced GPP. One family of fluids under consideration as alternatives to R-134a is the fluorinated propenes. Of particular interest is R-1234yf (2,3,3,3-tetrafluoropropene) which may be used on its own, or blended with other low GWP fluids such as $CF_3I$, to produce non-flammable mixtures with appropriate physical and thermophysical properties to be used in a number of the applications in which R-134a is currently used. Also of interest are refrigerant fluids comprising R-1225ye (1,1,1,2,3 pentafluoropropene), preferably absent $CF_3I$. Of interest are both isomeric forms of R-1225ye, namely the E and Z forms. R-1234yf, like the established HFCs, is a polar species and may be used in conjunction with PAG, PVE and ester lubricants currently used with R-134a or other HFC refrigerants. $CF_3I$ is relatively non-polar and may be used with traditional mineral oil or synthetic hydrocarbon lubricants. Blends comprising R-1234yf and $CF_3I$ may be used with PAG, PVE or ester lubricants or with traditional mineral oil or synthetic hydrocarbon lubricants.

There is therefore a need to provide a compatible desiccant material for use with R-1234yf or R-1225ye or with blends comprising R-1234yf and $CF_3I$. Further, there is a need to provide a desiccant that is compatible with R-1234yf, R-1225ye and blends containing R-1234yf and $CF_3I$, and an associated compressor lubricant.

According to the present invention, there is provided a method of drying a fluid comprising a fluoropropene, which method comprises the step of contacting the fluid with a desiccant comprising a molecular sieve having openings which have a size across their largest dimension of from about 3 Å to about 5 Å.

Preferably, the molecular sieve has openings which have a size across their largest dimension of from about 3 Å to about 4 Å.

Conveniently, the molecular sieve has openings which have a size across their largest dimension of about 4 Å.

Advantageously, the fluoropropene is R-1234yf, or R-1225ye, for example R-1225ye either in the thermodynamic or kinetic equilibrium blend of E and Z isomers, or relatively pure individual isomeric forms, e.g. greater than about 50%, conveniently greater than about 80%, conveniently greater than 90%, of the Z isomer, or greater than 50%, conveniently greater than 80%, conveniently greater than 90% E isomer.

Preferably, the fluid comprises at least one additional refrigerant component.

Conveniently, the at least one additional refrigerant component is selected from $CF_3I$, R-134a and R152a.

Advantageously, the fluid further comprises a lubricant.

Preferably, the lubricant is selected from esters, PAGs, PVEs, mineral oils and synthetic hydrocarbons.

Conveniently, the fluid further comprises a stabiliser.

Advantageously, the stabiliser is selected from epoxides, dienes and phenols.

Preferably, the fluid further comprises a dye.

Conveniently, the dye is a fluorescene.

Advantageously, the desiccant comprises at least one further desiccant or adsorbent other than the molecular sieve.

Preferably, the at least one further desiccant or adsorbent is selected from alumina, silica and activated carbon.

Conveniently, the desiccant does not contain any further desiccant other than the molecular sieve.

Advantageously, the fluid is a heat transfer fluid.

Preferably, the desiccant is contained in a cartridge.

According to a further aspect of the invention, there is provided a method of manufacturing a fluid comprising a fluoropropene, which method comprises a method of drying the fluid as defined herein.

According to another aspect of the invention, there is provided a method of providing cooling using a heat transfer fluid comprising a fluoropropene, which method comprises a method of drying the fluid as defined herein.

Preferably, the method of providing cooling is performed in a mobile air conditioning system.

Conveniently, the mobile air conditioning system is an automotive air conditioning system.

According to a further aspect of the invention, there is provided a heat transfer device comprising a heat transfer fluid comprising a fluoropropene, and a desiccant comprising a molecular sieve having openings which have a size across their largest dimension of from about 3 Å to about 5 Å.

Preferably, the heat transfer device is a refrigeration system.

Conveniently, the heat transfer device is an automotive air conditioning system.

DESCRIPTION OF THE DRAWING FIGURES

The invention will now be described, by way of example, with reference to the accompanying figure, in which;

FIG. 1 shows the levels of water in $CF_3I$ (TFIM), R-1234yf and R-134a, after drying with molecular sieves; and, FIG. 2 shows the capacity of desiccants in the drying of $CF_3I$ (TFIM), R-1234yf and R-134a.

DETAILED DESCRIPTION

We have surprisingly found that zeolite molecular sieve desiccants having nominal pore dimensions of below about 5 Å may be used with refrigerants comprising at least one fluoropropene, optionally blended with at least one additional refrigerant component. In particular we have found that zeolite molecular sieve desiccants having nominal pore dimensions of below about 5 Å may be beneficially used to remove moisture from R-1234yf or R-1225ye and blends of R-1234yf and R-1225ye with other refrigerant components, particularly R-134a, R-152a and/or $CF_3I$.

FIG. 1 represent the equilibrium water content of refrigerants in contact with a number of zeolite molecular sieves with nominal pore dimensions ranging from 3 Å (M3 Å) to 10 Å (MS13X). It is clear that as the nominal pore size of the molecular sieve increases, the water content of all of the refrigerants examined also increases, from approximately 0.003 mg $H_2O$ per mg of zeolite with the 3 Å zeolite to approximately 0.02 mg $H_2O$ per mg of zeolite with the 10 Å zeolite. Surprisingly, the 5 Å zeolite performs poorly with R-1234yf as the refrigerant, only achieving a water content comparable to that of the 10 Å zeolite. This is particularly surprising since the fluorinated propene would be expected to be larger than R-134a and so be expected to be less effectively absorbed by the 5 Å zeolite.

Also, WO01/83411 discloses the removal of (hydro) haloalkene impurities from product streams using a solid adsorbent. In particular, WO01/83411 describes the removal of R-1234yf from product streams using an adsorbent having a pore size of from about 7 Å to about 10 Å.

From the experimental results, we have found that in order to provide effective drying of refrigerant fluids comprising R-1234yf, a zeolite molecular sieve with a nominal pore dimension less than 5 Å is required. Because of the reduced water absorption rates associated with zeolite molecular sieves with nominal pore dimensions below about 3 Å, this value represents the lower end of the acceptable range of zeolite pore dimensions.

The poor performance of 5 Å pore zeolites is reflected in the corresponding molecular sieve water content represented in FIG. 2. Here, the 5 Å zeolite has a water content similar to that of the 10 Å system, approximately 0.08 mg $H_2O$ per mg of zeolite. In contrast, both R-134a and $CF_3I$ result in capacities of approximately 0.09 mg $H_2O$ per mg of zeolite. Clearly, a desiccant having a lower water capacity may still be used to dry a refrigerant fluid but would require a greater quantity to be used in order to absorb a set quantity of moisture from the fluid.

The desiccants of the invention are unlikely to act to remove additives such as stabilisers, dyes or lubricity enhancers from the circulating refrigeration fluid comprising a fluoropropene and a lubricant. In this way, the desiccants of the invention are unlikely to compromise the thermal stability of the refrigeration fluid or to compromise the performance of the compressor lubricant.

EXPERIMENTAL

Example 1

Zeolite molecular sieves 3 Å, 5 Å and 13X were purchased from Aldrich Chemical Company. The 4 Å XE molecular sieve was obtained from National Refrigeration Suppliers contained within spun-copper cartridges. Karl-Fischer titration for determining water content of the refrigerants was conducted on a Cou-Lo Compact instrument supplied by GRScientific.

A weighed quantity, approximately 0.4 g, of zeolite molecular sieve that had been previously dried in a stream of nitrogen gas at 150° C. for 12 hours, was placed in a stainless steel pressure vessel having an internal volume of 50 ml fitted with an access valve. The vessel valve was used to evacuate the vessel prior to introduction of a weighed quantity of liquid refrigerant, approximately 40 g, containing a known quantity, approximately 40 mg, of water. After initial mixing, the vessel was allowed to stand at approximately 23° C. for a period of 3 hours before a small sample of liquid refrigerant was removed from the vessel via the access valve and the water content determined by Karl-Fischer titration. The vessel was allowed to stand for a total of 24 hours to reach equilibrium before determining the water content of the refrigerant by removal of a further liquid sample.

To determine refrigerant moisture content, a sample of liquid refrigerant was passed through the access valve and allowed to evaporate within a length of stainless steel tubing leading to the Karl-Fischer titration cell. The resulting vapour was metered into the Karl-Fischer titration cell. Moisture content of the desiccant sample was calculated by difference.

Refrigerant moisture at. 24 hours (mg $H_2O$/g refrigerant)

|  | MS3A | MS4A | MS5A | MS13X |
|---|---|---|---|---|
| TFIM | 0.003 | 0.012 | 0.009 | 0.02 |
| R-1234yf | 0.003 | 0.01 | 0.021 | 0.019 |
| R-134a | 0.004 | 0.007 | 0.009 | 0.02 |

Sieve capacity at 24 hours (mg $H_2O$/mg sieve)

|  | MS3A | MS4A | MS5A | MS13X |
|---|---|---|---|---|
| TFIM | 0.097 | 0.088 | 0.091 | 0.08 |
| R-1234yf | 0.097 | 0.09 | 0.079 | 0.081 |
| R-134a | 0.096 | 0.093 | 0.091 | 0.08 |

MS13X molecular sieve has a 10Å nominal pore diameter. Preferred zeolites are those having pore sizes in the range of from about 3 Å to below about 5 Å, in particular, those having pore dimensions in the range of about. 3 Å to about 4 Å. Particular examples of commercially available zeolite molecular sieves falling within this preferred range include XH-7 and XH-9 manufactured by UOP, and MS594 and MS592 manufactured by Grace.

Example 2

In a variation of Example 1, wet R-1225ye was tested with a variety of molecular sieves and compared to R-134a.

In this experiment, the refrigerant was "wetted" by adding 0.5 g distilled water to an evacuated cylinder, to which was then added 250 g refrigerant. This mixture was allowed to equilibrate at room temperature for several hours before being analysed by Karl Fischer for liquid moisture contact.

The desiccant was prepared by drying it at 200° C. with dry nitrogen passing through it for at least 16 hours, 0.8 g desiccant was then added to a clear, dry cylinder which was then evacuated before adding 70 g of "wet" liquid refrigerant. This was then left at room temperature and analysed in duplicate providing an average value for liquid moisture after 3 and 24 hours.

| Time/Hrs | 3A | | | | 4A | | | | 5A | | | | 13X | | |
|---|---|---|---|---|---|---|---|---|---|---|---|---|---|---|---|
|  | 0 | 3 | 24 |  | 0 | 3 | 24 |  | 0 | 3 | 24 |  | 0 | 3 | 24 |
| R-134a | 769 | 382 | 31 | R-134a | 656 | 79 | 45 | R-134a | 816 | 132 | 70 | R-134a | 833 | 202 | 163 |
| R-1225ye | 641 | 275 | 55 | R-1225ye | 574 | 306 | 78 | R-1225ye | 598 | 329 | 181 | R-1225ye | 641 | 404 | 357 |

| 3A | mg water per mg sieve | mg water per g refrigerant |
|---|---|---|
| R-1225ye | 0.095 | 0.005 |
| R-134a | 0.096 | 0.004 |

| 5A | mg water per mg sieve | mg water per g refrigerant |
|---|---|---|
| R-1225ye | 0.084 | 0.016 |
| R-134a | 0.091 | 0.009 |

| 4A | mg water per mg sieve | mg water per g refrigerant |
|---|---|---|
| R-1225ye | 0.093 | 0.007 |
| R-134a | 0.093 | 0.007 |

| 13X | mg water per mg sieve | mg water per g refrigerant |
|---|---|---|
| R-1225ye | 0.069 | 0.031 |
| R-134a | 0.080 | 0.020 |

The results indicate an optimum sieve size of 3-4 Å; performance of sieves with a pore size greater than 4 Å is poor.

In certain embodiments, it may be beneficial to include another desiccant with the molecular sieve of the invention. Thus, in certain applications the desiccant material could comprise the molecular sieve alone, whilst other applications may use a desiccant that contains the molecular sieve in addition to one or more auxiliary agent such as alumina, silica and/or activated carbon, for example for the removal of acids.

The desiccant which is used in the process of the present invention comprises a molecular sieve containing pores having openings which have a size across their largest dimension in the range of from about 3 Å to about 5 Å, e.g. from greater than or equal to 3 Å to less than 5 Å. By opening we are referring to the mouth of the pore by which the molecule to be adsorbed enters the body of the pore where it becomes trapped. The openings to the pores may be elliptically shaped, essentially circular or even irregularly shaped, but will generally be elliptically shaped or essentially circular. When the pore openings are essentially circular, they should have a diameter in the range of from about 3 Å to about 5 Å, e.g. from greater than or equal to 3 Å to less than 5 Å.

Preferred adsorbents are those comprising pores having openings which have a size across their largest dimension in the range of from about 3 Å to about 4 Å.

The desiccant may contain more than one distribution of pore sizes, so that in addition to the pores of the required dimension in which the openings to the pores have a size across their largest dimension in the range of from 3 Å to 5 Å, the adsorbent, may also contain pores which are either larger or smaller. Thus, the adsorbent does not have to contain exclusively pores within the 3 Å to 5 Å range. However, any pores outside this range will not be as effective at selectively removing moisture from the fluoropropenes.

The desiccant should be in particulate form and is conveniently in the form of pellets or beads. When used in the manufacture of fluoropropenes, the particulate adsorbent is typically arranged as a bed or layer in an adsorption tower or column and the product stream may be conveyed over or through the bed. The desiccant bed may be a fluidised or moving bed, but in a preferred embodiment is a fixed or static bed. When used to dry the circulating fluid in a refrigeration system, the desiccant is conveniently in the form of pellets or beads contained within a cartridge, through which liquid refrigerant, containing any circulating compressor lubricant, is passed. Alternatively, the desiccant may be in the form of a solid, porous core comprising a zeolite of the present invention, a binder and any auxiliary desiccants or adsorbents such as silica gel, alumina or activated carbon. In use, the core is contained within a cartridge and the circulating refrigeration fluid is caused to pass through the cartridge and into contact with the core.

The desiccant typically has a surface area in the range of from 300 to 900 m²/g.

The desiccant is normally ore-treated prior to use by heating in a dry gas stream, such as dry air or dry nitrogen. This process is known to those skilled in the art and has the effect of activating the desiccant.

Typical temperatures for the pre-treatment are in the range of from 100 to 400° C.

The process of the present invention can be conducted with the product stream in the liquid phase or the vapour phase. In a fluoropropene manufacturing process, the product stream exiting the reactor will typically be pre-treated before it is subjected to the process of the present invention in order to reduce the overall level of impurities in the product stream. This pre-treatment will typically include a distillation step. The product stream may also be re-circulated and conducted several times through the same adsorbent bed in order to achieve the desired low level of water.

The process of the invention may be operated in a batch or continuous manner, although continuous operation is preferred.

The present process is preferably operated at a temperature in the range of from −20 to 100° C., more preferably in the range of from 10 to 70° C. and particularly in the range of from 10 to 50° C.

The preferred operating pressures are in the range of from 1 to 30 bar, more preferably in the range of from 5 to 20 bar and particularly in the range of from 6 to 12 bar.

The preferred feed rate for the product stream to the desiccant bed is in the range of from 0.1 to 50 hour$^{-1}$, more preferably in the range of from. 1 to 30 hour$^{-1}$ for liquid phase product streams and in the range of from 10 to 10,000 hour$^{-1}$, more preferably in the range of from 100 to 5,000 hour$^{-1}$ for vapour phase product streams.

During operation of the present process, the adsorption capability of the desiccant is gradually consumed as the pores become occupied with water. In the manufacture of fluoropropenes, the ability of the adsorbent to adsorb water will eventually be substantially impaired and at this stage the adsorbent must be regenerated. Regeneration is typically effected by heating the used adsorbent in a dry gas stream, such as dry air or dry nitrogen, at a temperature in the range of from. 100 to 300° C., e.g. 100 to 200° C., and a pressure in the range of from 1 to 30 bar, e, g. 5 to 15 bar. This process is known to those skilled in the art. When used in refrigeration systems, the desiccant cartridge or core is normally replaced on exhaustion of the water absorption capacity of the desiccant or as part of a routine service.

We claim:

1. A method of drying a fluid comprising a fluoropropene and water, the method comprises the step of:
   contacting the fluid with a desiccant comprising a molecular sieve having openings which have a size across their largest dimension of from 3 Å to 5 Å,
   wherein the ratio by weight of desiccant to fluid is greater than 1:100.

2. The method according to claim 1 wherein the molecular sieve has openings which have a size across their largest dimension of from 3 Å to 4 Å.

3. The method according to claim 2 wherein the molecular sieve has openings which have a size across their largest dimension of about 4 Å.

4. The method according to claim 1 wherein the fluoropropene is R-1234yf or R-1225ye.

5. The method according to claim 4 wherein the fluid comprises at least one additional refrigerant component.

6. The method according to claim 5 wherein the at least one additional refrigerant component is selected from $CF_3I$, R-134a and R152a.

7. The method according to claim 4 wherein the fluid further comprises a lubricant.

8. The method according to claim 7 wherein the lubricant is selected from the group consisting of esters, PAGs, PVEs, mineral oils and synthetic hydrocarbons.

9. The method according claim 1 wherein the fluid further comprises a stabilizer.

10. The method according to claim 9 wherein the stabiliser is selected from epoxides, dienes and phenols.

11. The method according to claim 1 wherein the fluid further comprises a dye.

12. The method according to claim 11 wherein the dye is a fluorescene.

13. The method according to claim 1 wherein the desiccant comprises at least one further desiccant or adsorbent other than the molecular sieve.

14. The method according to claim 13 wherein the at least one further desiccant or adsorbent is selected from alumina, silica and activated carbon.

15. The method according to claim 14 wherein the desiccant is contained in a cartridge.

16. The method according to claim 1 wherein the desiccant does not contain any further desiccant other than the molecular sieve.

17. The method according to claim 1 wherein the fluid is a heat transfer fluid.

18. A method of providing cooling, the method comprising:

providing a heat transfer fluid comprising a fluoropropene and water;

drying the fluid by contacting the heat transfer fluid with a desiccant, said desiccant comprising a molecular sieve having openings which have a size across their largest dimension of from 3 Å to 5 Å; and using the fluid to provide cooling, wherein the ratio by weight of desiccant to fluid is greater than 1:100.

19. A heat transfer device comprising:

a heat transfer fluid comprising a fluoropropene and;

and a desiccant comprising a molecular sieve having openings which have a size across their largest dimension of from 3 Å to 5 Å, wherein said molecular sieve is designed to remove water from said heat transfer fluid, wherein the ratio weight of desiccant to fluid is greater than 1:100.

20. The heat transfer device according to claim 19 wherein the heat transfer device is a refrigeration system, and wherein said fluoropropene is R-1234yf.

21. The method of claim 1, wherein the ratio by weight of desiccant to fluid is greater than 1:87.5.

* * * * *